US008869802B2

(12) United States Patent
Wilson et al.

(10) Patent No.: US 8,869,802 B2
(45) Date of Patent: Oct. 28, 2014

(54) DISC ANNULUS CLOSURE

(75) Inventors: Jeffrey A. Wilson, Wrentham, MA (US); Michael T. Milbocker, Holliston, MA (US); Robert M. Arcangeli, Westborough, MA (US)

(73) Assignee: Promethean Surgical Devices, LLC, East Hartford, CT (US)

( * ) Notice: Subject to any disclaimer, the term of this patent is extended or adjusted under 35 U.S.C. 154(b) by 0 days.

(21) Appl. No.: 13/086,754

(22) Filed: Apr. 14, 2011

(65) Prior Publication Data

US 2011/0306982 A1  Dec. 15, 2011

Related U.S. Application Data

(63) Continuation of application No. 12/575,638, filed on Oct. 8, 2009, now abandoned, which is a continuation of application No. 12/152,389, filed on May 14, 2008, now abandoned.

(60) Provisional application No. 60/931,407, filed on May 22, 2007, provisional application No. 60/930,064, filed on May 14, 2007, provisional application No. 60/930,104, filed on May 14, 2007.

(51) Int. Cl.
*A61B 17/56* (2006.01)
*A61F 2/30* (2006.01)
*A61F 2/44* (2006.01)

(52) U.S. Cl.
CPC ....... *A61F 2/442* (2013.01); *A61F 2002/30733* (2013.01); *A61F 2002/30069* (2013.01); *A61F 2002/30586* (2013.01); *A61F 2002/444* (2013.01); *A61F 2002/3092* (2013.01)
USPC .......................................... 128/898; 606/279

(58) Field of Classification Search
USPC ........... 128/898; 604/103.01, 103.03, 103.05, 604/104, 110; 606/92–94, 192, 213, 279; 623/17.11–17.16
See application file for complete search history.

(56) References Cited

U.S. PATENT DOCUMENTS

| 4,804,691 | A | | 2/1989 | English et al. |
| 5,156,613 | A | | 10/1992 | Sawyer |
| 5,269,785 | A | * | 12/1993 | Bonutti .......................... 606/80 |
| 5,308,325 | A | * | 5/1994 | Quinn et al. ............... 604/96.01 |
| 5,571,117 | A | | 11/1996 | Ahn |
| 6,077,216 | A | | 6/2000 | Benderev et al. |
| 6,110,101 | A | | 8/2000 | Tihon et al. |
| 6,123,667 | A | | 9/2000 | Poff et al. |

(Continued)

FOREIGN PATENT DOCUMENTS

WO    WO 2007089484 A2 *   8/2007 .............. A61L 27/18

*Primary Examiner* — Nicholas Woodall
*Assistant Examiner* — Larry E Waggle, Jr.
(74) *Attorney, Agent, or Firm* — Novak Druce Connolly Bove + Quigg LLP; Carol L. Bunner

(57) ABSTRACT

Disclosed herein are methods for treating a defect in a spinal disc nuclear space, comprising: (a) creating an opening by open, percutaneous or laparoscopic techniques to access the defect in the nuclear space; (b) removing a desired amount of tissue from the nuclear space; (c) positioning a delivery catheter through the opening; (d) fluidically isolating the nuclear space by blocking the opening with a blocking component of the catheter; (e) delivering an in-situ curable liquid material through a lumen of the catheter to the nuclear space; and (f) maintaining the isolating until the liquid material has cured. Also disclosed are treatment systems and materials for prostheses.

27 Claims, 8 Drawing Sheets

(56) References Cited

U.S. PATENT DOCUMENTS

| | | |
|---|---|---|
| 6,197,036 B1 | 3/2001 | Tripp et al. |
| 6,211,335 B1 | 4/2001 | Owen et al. |
| 6,221,005 B1 | 4/2001 | Bruckner et al. |
| 6,265,016 B1 | 7/2001 | Hostettler et al. |
| 6,296,607 B1 | 10/2001 | Milbocker |
| 6,334,446 B1 | 1/2002 | Beyar |
| 6,382,214 B1 | 5/2002 | Raz et al. |
| 6,502,578 B2 | 1/2003 | Raz et al. |
| 6,503,190 B1 | 1/2003 | Ulmsten et al. |
| 6,669,654 B2 | 12/2003 | Diokno et al. |
| 2002/0049503 A1* | 4/2002 | Milbocker ............... 623/23.72 |
| 2003/0135238 A1 | 7/2003 | Milbocker |
| 2004/0068078 A1 | 4/2004 | Milbocker |
| 2004/0097924 A1* | 5/2004 | Lambrecht et al. ............ 606/60 |
| 2005/0070913 A1* | 3/2005 | Milbocker et al. ............ 606/92 |
| 2005/0113923 A1* | 5/2005 | Acker et al. ............... 623/17.12 |
| 2005/0187556 A1* | 8/2005 | Stack et al. ................. 606/79 |
| 2006/0004457 A1* | 1/2006 | Collins et al. ............. 623/17.16 |
| 2006/0149380 A1* | 7/2006 | Lotz et al. ............... 623/17.12 |
| 2006/0253198 A1* | 11/2006 | Myint et al. ............. 623/17.12 |

* cited by examiner

DISC ANNULUS CLOSURE

RELATED APPLICATIONS

This application is a continuation of and claims priority under 35 U.S.C. §120 to U.S. Ser. No. 12/575,638, filed Oct. 8, 2009 now abandoned which is a continuation of U.S. Ser. No. 12/152,389, filed May 14, 2008 now abandoned, and claims the benefit of priority under 35 U.S.C. §119(e) to U.S. Provisional Application Nos. 60/931,407, filed May 22, 2007, 60/930,064, filed May 14, 2007 and 60/930,104, filed May 14, 2007, the disclosures of which are incorporated herein by reference.

FIELD OF THE INVENTION

This disclosure relates to methods and devices for modifying intervertebral disc tissue, spaces, and structure. Also disclosed are methods and devices disclosed relate to the localization of an in situ forming nucleus replacement prosthetic, while it is fluid and not fully cured, using open and minimally invasive techniques. The devices for localizing the in situ curing implant are catheter-based, and adapt their cross section to occlude the otomy to the disc nucleus while providing for catheter delivery of the fluid implant.

BACKGROUND OF THE INVENTION

Intervertebral disc abnormalities are common in the population and cause considerable pain, particularly if they affect adjacent nerves. Disc abnormalities result from trauma, wear, metabolic disorders and the aging process and include degenerative discs, localized tears or fissures in the annulus fibrosus, localized disc herniations with contained or escaped extrusions, and chronic, circumferential bulging discs. Disc fissures occur as a degeneration of fibrous components of the annulus fibrosus. Rather minor activities such as sneezing, bending or simple attrition can tear degenerated annulus fibers and create a fissure. The fissures may be further complicated by extrusion of nucleus pulposus material into or beyond the annulus fibrosus. Difficulties can still present even when there is no visible extrusion, due to biochemicals within the disc irritating surrounding structures and nerves.

A contained disc herniation is not associated with free nucleus fragments migrating to the spinal canal. However, a contained disc herniation can still protrude and irritate surrounding structures, for example by applying pressure to spinal nerves. Escaped nucleus pulposus can chemically irritate neural structures. Current treatment methods include reduction of pressure on the annulus by removing some of the interior nucleus pulposus material by percutaneous nucleotomy. See, for example, Kambin U.S. Pat. No. 4,573,448. Complications include disc space infection, nerve root injury, hematoma formation, instability of the adjacent vertebrae and collapse of the disc from decrease in height. It has been proposed to treat weakening due to nucleus pulposus deficiency by inserting preformed hydrogel implants. See, Ray U.S. Pat. Nos. 4,772,287; 4,904,260 and, 5,562,736 and Bao U.S. Pat. No. 5,192,326.

More recently, delivery of in situ curing liquids to form a solid prosthetic in the nucleus of a disc have been disclosed. The fluid form of these implants enables access to the spine in a minimally invasive manner, and includes procedures for restoring structural integrity to vertebral bodies. See Scribner U.S. Pat. Nos. 6,241,734 and 6,280,456; Reiley U.S. Pat. Nos. 6,248,110 and 6,235,043; Boucher U.S. Pat. No. 6,607,554 and Bhatnagar U.S. Pat. No. 6,395,007. Methods of repairing the spinal disc or portions thereof are disclosed in Cauthern U.S. Pat. No. 6,592,625, Haldimann U.S. Pat. No. 6,428,576, Trieu U.S. Pat. No. 6,620,196 and Milner U.S. Pat. No. 6,187,048.

There are a variety of injectable biomaterials disclosed in issued patents including: cross-linkable silk elastin copolymer disclosed in Stedronsky U.S. Pat. No. 6,423,333, Capello U.S. Pat. No. 6,380,154, Ferrari U.S. Pat. No. 6,355,776, Stedronsky U.S. Pat. No. 6,258,872, Ferrari U.S. Pat. No. 6,184,348, Ferrari U.S. Pat. No. 6,140,072; Stedronsky U.S. Pat. No. 6,033,654; Ferrari U.S. Pat. No. 6,018,030; Stedronsky U.S. Pat. No. 6,015,474; Ferrari U.S. Pat. No. 5,830,713; Stedronsky U.S. Pat. No. 5,817,303; Donofrio U.S. Pat. No. 5,808,012; Capello U.S. Pat. No. 5,773,577; Capello U.S. Pat. No. 5,773,249; Ferrari U.S. Pat. No. 5,770,697; Stedronsky U.S. Pat. No. 5,760,004; Donofrio U.S. Pat. No. 5,723,588; Ferrari U.S. Pat. No. 5,641,648; Capello U.S. Pat. No. 5,235,041; protein hydrogel described in Morse U.S. Pat. No. 5,318,524; Morse U.S. Pat. No. 5,259,971; Morse U.S. Pat. No. 5,219,328; polyurethane-filled balloons disclosed in Bao U.S. Pat. No. 7,077,865; Bao U.S. Pat. No. 7,001,431; Felt U.S. Pat. No. 6,306,177; Felt U.S. Pat. No. 6,248,131; Bao U.S. Pat. No. 6,224,630; collagen-PEG disclosed in Olsen U.S. Pat. No. 6,428,978; Olsen U.S. Pat. No. 6,413,742; Rhee U.S. Pat. No. 6,323,278; Wallace U.S. Pat. No. 6,312,725; Sierra U.S. Pat. No. 6,277,394; Rhee U.S. Pat. No. 6,166,130; Berg U.S. Pat. No. 6,165,489; Simonyi U.S. Pat. No. 6,123,687; Berg U.S. Pat. No. 6,111,165; Sierra U.S. Pat. No. 6,110,484; Prior U.S. Pat. No. 6,096,309; Rhee U.S. Pat. No. 6,051,648; Esposito U.S. Pat. No. 5,997,811; Berg U.S. Pat. No. 5,962,648; Rhee U.S. Pat. No. 5,936,035; Rhee U.S. Pat. No. 5,874,500; chitosan disclosed in Chemte U.S. Pat. No. 6,344,488; other polymers discussed in Boyd U.S. Pat. No. 7,004,945; Collins U.S. publication 2006/0004326; Collins U.S. publication 2006/0009851; Milner U.S. Pat. No. 6,187,048; Daniell U.S. Pat. No. 6,004,782; Urry U.S. Pat. No. 5,064,430; Urry U.S. Pat. No. 4,898,962; Urry U.S. Pat. No. 4,870,055; Urry U.S. Pat. No. 4,783,523; Urry U.S. Pat. No. 4,589,882; Urry U.S. Pat. No. 4,500,700; Urry U.S. Pat. No. 4,474,851; Urry U.S. Pat. No. 4,187,852; Urry U.S. Pat. No. 4,132,746.

Delivery of an in situ forming prosthetic to the nuclear space requires constructing a passageway into the nucleus and removal of the nucleus fibrosus, in total or in part. The passageway is usually made through the annulus, especially when part of the annulus should be removed to correct a pathological condition. Whether the passageway is through the annulus or elsewhere, for example, through the vertebral body, there is a risk of the formed nucleus prosthetic extruding through the passageway. Nucleus prosthetic extrusion can affect the surrounding nerves adversely. Methods of blocking a passageway made through the annulus are disclosed in Lambrecht U.S. Pat. No. 6,425,919, Lambrecht, et al. U.S. Pat. No. 6,482,235, Lambrecht, et al. U.S. Pat. No. 6,508,839, Cauthen U.S. Pat. No. 6,592,625, Lambrecht, et al. U.S. Pat. No. 6,821,276 and Lambrecht et al. U.S. Pat. No. 6,883,520. Other methods of preventing nucleus prosthetic extrusion include enclosing the prosthetic entirely inside of an enveloping sheath and are disclosed in Ray, et al. U.S. Pat. No. 4,904,260, Bao, et al. U.S. Pat. No. 5,192,326, Kuslich U.S. Pat. No. 5,549,679, Stalcup, et al. U.S. Pat. No. 6,332,894, Wardlaw U.S. Pat. No. 6,402,784, Weber, et al. U.S. Pat. No. 6,533,818, and Reuter, et al. U.S. Pat. No. 6,805,715. Still other methods of preventing nuclear prosthetic extrusion include delivering a preformed prosthetic in a reduced state, which when introduced into the body increases in volume. These methods and devices are disclosed in Ray, et al. U.S.

Pat. No. 6,602,291, Stoy, et al. U.S. Pat. No. 6,726,721, and Li, et al. U.S. Pat. No. 6,764,514.

None of the techniques or devices and associated methods of their use described above are entirely satisfactory from either a biocompatibility or efficacy perspective, for localization of an in situ curing liquid nucleus implant. Accordingly, there remains a need for the development of treatment methods and devices for implanting spinal disc prostheses.

SUMMARY OF THE INVENTION

One embodiment provides a method for treating a defect in a spinal disc nuclear space, comprising:

(a) creating an opening by open, percutaneous or laparoscopic techniques to access the defect in the nuclear space;

(b) removing a desired amount of tissue from the nuclear space;

(c) positioning a delivery catheter through the opening;

(d) fluidically isolating the nuclear space by blocking the opening with a blocking component of the catheter;

(e) delivering an in-situ curable liquid material through a lumen of the catheter to the nuclear space; and (f) maintaining the isolating until the liquid material has cured.

BRIEF DESCRIPTION OF THE DRAWINGS

Various embodiments of the invention will be understood from the following description, the appended claims and the accompanying drawings, in which:

DETAILED DESCRIPTION

Figure 1:
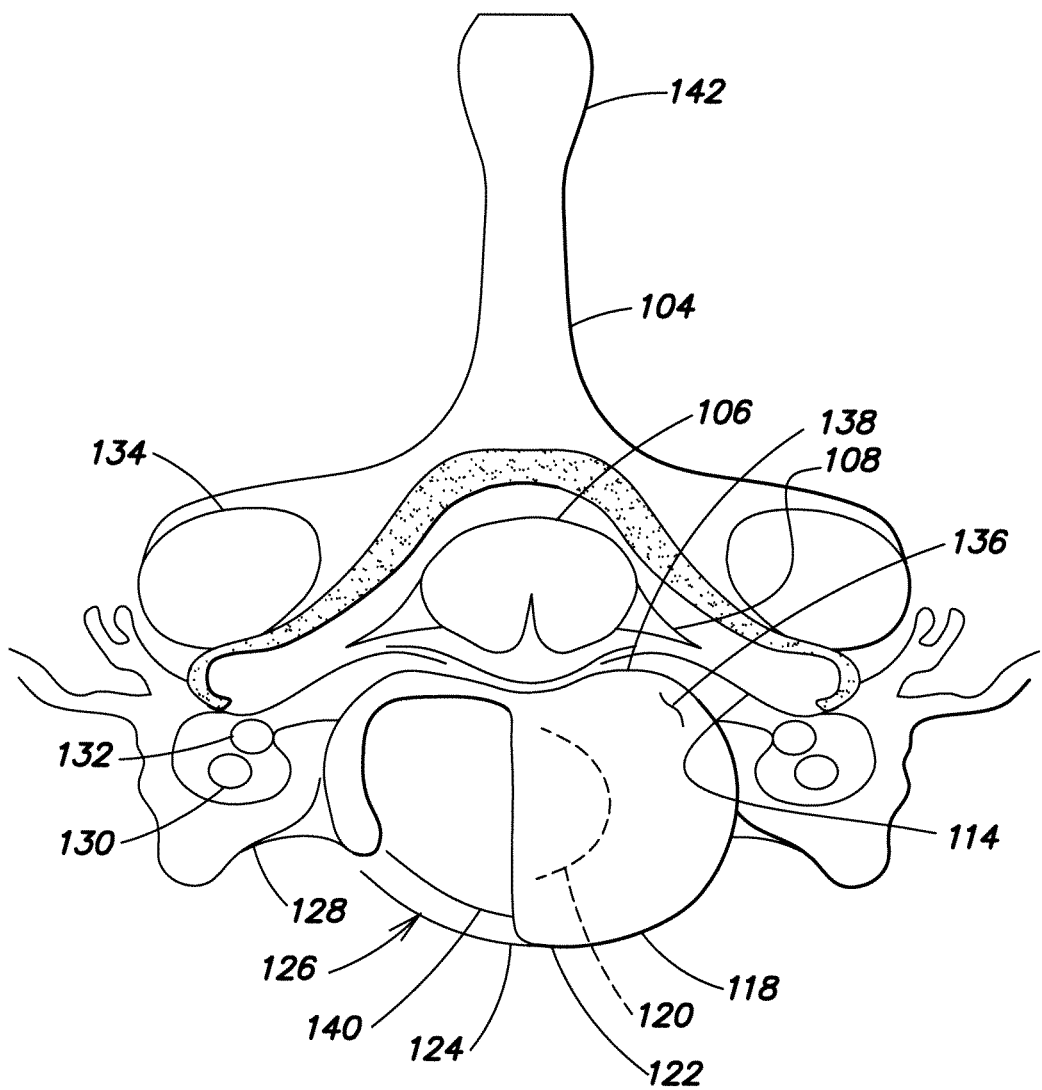
FIG. 1 is a superior cross sectional anatomical view of a cervical disc and vertebra.

One embodiment provides a device for delivering an in situ curing liquid nucleus implant intended to replace or augment the natural disc nucleus space. The disc nucleus space includes the nucleus pulposus and the adjacent tissues, including the vertebral endplates and inner layers of the disc annulus. Curing with respect to the liquid nucleus implant refers to a phase change of the implant from liquid to solid. The treatment involves delivery of an in situ polymerizing tissue adhesive into the treatment area of the nucleus or nuclear space. The treatment further involves a means for preventing migration of the liquid implant after it has been delivered and before it has fully cured. The delivery aspects of the device are not intended to remain in the body after the implant has been delivered and cured.

One embodiment provides a method for treating a defect in a spinal disc nuclear space, comprising:

(a) creating an opening by open, percutaneous or laparoscopic techniques to access the defect in the nuclear space;

(b) removing a desired amount of tissue from the nuclear space;

(c) positioning a delivery catheter through the opening;

(d) fluidically isolating the nuclear space by blocking the opening with a blocking component of the catheter;

(e) delivering an in-situ curable liquid material through a lumen of the catheter to the nuclear space; and (f) maintaining the isolating until the liquid material has cured.

In one embodiment, the removing in (b) comprises removing one of (i) a portion of the nucleus pulposus, (ii) all of the nucleus pulposus, or (iii) a portion or all of the nucleus pulposus and a portion or all of the inner layers of the annulus fibrosus.

In one embodiment, the device or delivery catheter comprises a lumen, typically of minimal cross section, but sufficiently large to deliver the liquid nucleus implant by conventional methods. Conventional methods include a syringe or similar liquid dispensing device that is either mechanically pressurized or manually pressurized sufficiently to deliver the liquid nucleus implant to the treatment site before the liquid implant has cured. In one embodiment, the delivery lumen, conventionally a catheter, is fitted with a syringe-type connection, such as a luer connection.

In one embodiment, the delivery catheter comprises a blocking component that sealably interfaces with the access hole made through bone or the disc annulus. In one embodiment, the blocking component is inflatable, e.g., a balloon surrounding a catheter, where the catheter possesses at least one lumen for delivery of the liquid nucleus implant and a least one lumen for controllably inflating the balloon.

In another embodiment, where the blocking aspect is an elastic collar made to expand by compression along the delivery catheter only one lumen is required.

In one embodiment, the treatment method comprises two or more applications of in-situ curable liquid material. The delivery lumen may be suitably sized to allow a tube to be inserted in the delivery lumen to act as a disposable delivery lumen to be removed after a first delivery of liquid material has cured and to be subsequently replaced by an additional disposable delivery lumen to enable a second delivery of liquid implant. This process can be repeated for as many applications of liquid material desired.

In one embodiment, the proximal and distal ends of the blocking component may be marked with radio-opaque features or other marker suitable for enabling a medical professional to position the blocking aspect relative to a vertebral feature. In another embodiment, a set of proximal and distal markers suitable for positioning the blocking component in the nucleus annulus provides the proximal end flush with the inner surface of the annulus or on the margin of a cleared region of nucleus.

In one embodiment, the treating comprises one or more of:

(i) augmenting or replacing the nucleus pulposus;

(ii) reinforcing a wall of the annulus fibrosus;

(iii) removing and sealing herniated or bulging portions of a disc; and (iv) closing a defect in the annulus pulposus.

One embodiment provides techniques employing the in situ curing liquid nucleus implant delivery device for modifying the disc annulus, vertebral endplates and/or nucleus to restore nuclear integrity. Open and minimally invasive surgical methods can be used to treat disc abnormalities at locations previously not accessible via percutaneous approaches, and without substantial destruction of the disc and/or surrounding tissue. The treatment entails delivery of in-situ curable liquid material to select locations within the disc, including delivery to the location of an annular fissure, the location of a nuclectomy, or the location of an annulus herniation. In one embodiment, the surgical methods disclosed herein involve producing an access to the nucleus pulposus, and delivering an in situ phase-changing liquid to repair the annulus, endplates and/or nucleus.

Establishing the access to the nucleus pulposus may involve a positioning means comprising a needle or guidewire which is directed to a treatment site in the disc, guiding a cutting device to the site where the positioning means is located so as to make an access through the annulus or bone, and delivering along the positioning means an operational port through which the delivery catheter might be deployed. In the case of access through the disc annulus, the operational port may accommodate a conically terminated stylet suitable for delivering the operational port in a minimally disruptive manner to a site within the disc. Once positioned, the conically terminated stylet is removed and a portion or all of the nucleus pulposus may be removed by conventional means through this port. Once a sufficient quantity of nucleus is removed the delivery catheter is positioned within the operational port such that when the blocking means is deployed, liquid nucleus implant may be injected into the created nuclear space such that the implant material is prevented from traversing the operational port.

In one embodiment, the delivery catheter does not require a second lumen for removal of the displaced gas where the implant foams and encapsulates the air at an elevated pressure. Alternatively, an overflow or gas displacement port situated in either the operational port or the delivery catheter may be employed in the design. Once the liquid implant is cured the catheter and operational port may be removed from the body leaving the cut surfaces of the annulus free from implant material and thus disposed to grow together through the natural healing process.

In a further embodiment, it is contemplated that the in-situ curing nucleus implant may be introduced into the nucleus (which may be previously evacuated by nucleotomy) to form a reinforced nucleus implant in-situ. Additional nucleus implant may be introduced at the same time or subsequent to curing of the initial insertion by removing the delivery catheter only and repositioning a fresh delivery catheter in the operational port.

In another embodiment, the method further comprises:
(g) removing the blocking component and the delivery catheter; and
(h) closing the opening.

In one embodiment, the proposed methods generally involve one or more of the following steps:
1. Creating an opening by open, percutaneous posterior-lateral, retroperitoneal, or anterior laparoscopic method. Accessing a desired portion of spinal disc region through an operational port can occur in a minimally invasive manner and under the assistance of a guide wire. The surgical approach selected may vary depending upon the portion of the spinal disc segment to be treated.
2. Optionally, removing diseased or degenerated tissue while minimizing removal of healthy tissue while (e.g. removing bulging portions of the annulus fibrosis, or nucleus pulposis, removal of osteophytes, etc.)
3. Positioning a delivery catheter through the opening. The positioning can comprise placing the operational port in the disc annulus by means of insertion of a conical stylet into the operational port, advancing the operational port into the disc annulus, removal of the conical stylet, and insertion of a delivery catheter.
4. Fluidically isolating the nuclear space by blocking the opening with a blocking component of the catheter, (actuation of the blocking means).
5. Delivering an in-situ curable liquid material (e.g., a polymerizing nucleus implant) through a lumen of the delivery catheter and into the nuclear space. The delivering can comprise replacing all or a portion of the disc nucleus (which may have previously been removed during the same or prior surgery) with the in-situ curable liquid (polymerizing fluid).
6. Maintaining the isolating until the liquid material/implant has cured. Upon curing, the method can comprise removing the delivery catheter by deactuation of the blocking means, retracting the operational port or optionally introducing another delivery catheter for a second delivery of liquid polymer and repeating the above steps until suitable replacement and augmentation of the disc nucleus is achieved.
7. Retracting the operational port from the disc annulus, stopping just outside the disc annulus and optionally providing a closure means to the otomy (i.e., the surgically created opening) of the disc annulus and finally removing the operational port from the body.
8. Closing any openings created to gain access to the spine.

In addition to the method, there is provided an in-situ curable liquid material (a liquid nucleus implant) sufficient to provide the therapeutic effect of strengthening and/or filling the intervertebral space and preventing extrusion of the polymerized prosthetic. A variety of in-situ polymerizing liquids may be used, both adhesive and non-adhesive. In one embodiment, the in-situ polymerizing liquid is a single-component polyisocyanate based adhesive as described in U.S. Pat. Nos. 6,254,327, 6,296,607, U.S. provisional patent application Ser. No. 60/557,314, and U.S. Pub. Nos. 2003/0135238 and 2005/0215748, the disclosures of which are incorporated herein by reference in its entirety.

Another embodiment provides a device that has a distal end fitted with a detachable bag that is inserted into the disc and accesses the posterior, posterior lateral and the posterior medial regions of the inner wall of the annulus fibrosus in order to repair an annular fissure at such a location by filling the bag with adhesive.

The present invention generally provides methods and apparatus for treating intervertebral disc disorders by delivering a liquid nucleus implant through a delivery catheter to the spinal disc space. The liquid implant can be delivered within the disc nucleus to repair or replace the nucleus through a delivery catheter containing a blocking component to contain or prevent escape of extrusions. The liquid nucleus implant and delivery catheter may also be used to create a disc nucleus implant in-situ. In one embodiment, the methods and devices are used to deliver and reinforce a single-part in-situ polymerizing nucleus implant to accomplish the desired surgical results.

In one embodiment, a liquid in situ curing agent is delivered via a delivery catheter with a blocking component for fluidically isolating, accessing, and delivering an in-situ curing agent to a location in an intervertebral disc having an annulus fibrosus, the annulus having an inner wall. Additionally, certain embodiments can be used with any of a variety of insertional apparatus to provide proximity to the disc, such as insertional apparatus known in the art as "introducers". In one embodiment, the delivery catheter comprises a lumen that fits snugly to the inner surface of the introducer and provides sufficient frictional retaining and blocking force to remain localized in the introducer during injection of the liquid nucleus implant. An introducer has an internal lumen with a distal opening at a terminus of the introducer to allow insertion/manipulation of the operational parts of the delivery catheter in the interior of a disc.

In one embodiment, the blocking component isolates the tissues surrounding the opening in the annulus from the liquid implant placed in the nuclear space to provide for the unobstructed growth of the annulus into the space created by the opening. In one embodiment, the inner wall of the annulus fibrosus can include the young wall comprised primarily of fibrous material as well as the transition zone, which includes both fibrous material and amorphous colloidal gels.

In one embodiment, after the removing in (b), a sheet is interposed between the nuclear space and the blocking component to provide increased strength to the cured liquid implant after it has cured. Exemplary sheets include those described in U.S. Pat. No. 7,044,982 and U.S. Pub. Nos. 2006/0233852, the disclosure of which is incorporated herein by reference.

The relevant anatomy is illustrated in FIG. 1, which illustrates a cross sectional view of the anatomy of a vertebra and associated disc. Structures of a typical cervical vertebra (superior aspect) are shown in FIG. 1: 104—lamina; 106—spinal cord; 108—dorsal root of spinal nerve; 114—ventral root of spinal nerve; 118—intervertebral disc; 120—nucleus pulposus; 122—annulus fibrosus; 124—anterior longitudinal ligament; 126—vertebral body; 128—pedicle; 130—vertebral artery; 132—vertebral veins; 134—superior articular facet; 136—posterior lateral portion of the annulus; 138—posterior medial portion of the annulus; 140—vertebral plate, and 142—spinous process. In FIG. 1, one side of the intervertebral disc 118 is not shown so that the anterior vertebral body 126 can be seen.

Liquid Nucleus Implants

One embodiment provides methods for use of a liquid nucleus implant to repair defects in a disc, including repair of the annulus and/or filling of a nuclear space. Regarding the nucleus implant, a liquid material is introduced into the intervertebral space to improve the function of the disc tissues and fluids contained therein. In one embodiment, the liquid nucleus implant has a low viscosity and is capable of delivery through a small diameter needle, cannula or catheter, for example through a typical catheter having an inner diameter ranging from 3.5 to 5 mm (but smaller diameter devices can be used if viscosity is sufficiently low.) Low viscosity can be useful in one or more of the following: 1) ease of delivery, 2) timely delivery, 3) prevention of delayed pressure transference from source to the target tissue site, and 4) permits sensing of resistance feedback by the operator to determine appropriate delivery volumes.

In one embodiment, the viscosity of the curable liquid material is less than 1000 cp, such as an implant viscosity of less than 200 cp. In another embodiment, the viscosity ranges from 100 cp to 1000 cp. In one embodiment, the viscosity limit of 1000 cp is satisfied when prepolymer is mixed with water in the ratio of 70:30 or less, and 60:40 or less for the 200 cp limit.

In one embodiment, the liquid nucleus implant is a single-component, self-curing adhesive that polymerizes in-situ forming internal cross links as well as bonds to surrounding tissue and bone. A single-component implant is one in which the composition of the implant is substantially the same during all phases of delivery; and, specifically is not an implant that has more than one tissue reactive component. A single-component implant may be mixed with one or more dilutive agents to aid in implant delivery provided the ratio of diluent to active component is not critical to the curing of the implant. An implant component is any combination of chemical species that can be stored at room temperature without substantial chemical change and remain homogenous in combination. For example, sodium chloride and water when mixed form an implant component commonly known as saline. Specifically, a single-component implant may be a mixture of any number of implant components provided only one is tissue reactive. A tissue reactive implant component is any implant component with a tissue biocompatibility as assessed by ISO 10993 different from that of physiologic saline.

In one embodiment, the single-component in-situ curable liquid material comprises a prepolymer An example of a single-component in situ polymerizing implant is one in which polymerization of the prepolymer, which can be a tissue reactive component, is initiated either by aqueous fluids present in the tissue or by addition of physiological saline or other inert medicinal solution before delivery to the target site. In one embodiment, the polymerization of a single-component implant does not require the addition of cross linkers, catalysts, chain extenders, or complementary components of an adhesive composition. In one embodiment, cross linking and tissue bonding is mediated either by aqueous fluids present in the tissue, or by premixing of the adhesive with physiological saline or other medicinal saline solution at the time of administration. The polymerization time of adhesives is variable, and can be in the range of about 30 seconds to 30 minutes or more, depending on the application. Exemplary prepolymers are described in U.S. Pat. No. 6,254,327, and U.S. Pub. Nos. 2003-0135238 and US 2004-0068078, the disclosures of which are incorporated herein by reference.

Polymerization time can be adjusted by selection of properties and components of the liquid nucleus implant. In one embodiment, the tissue reactive single component is a liquid comprising a polyisocyanate-capped polyol, typically macromolecular in size, having a mean molecular weight of about 1000 Daltons or more, more typically at least about 4000 Daltons, and yet more typically in a range of about 4500 D to about 10,000 D, depending on application. Higher molecular weight macromers may be of use in adhesives having great pliability (and lower tensile strength). In another embodiment, the liquid nucleus implant further comprises a low-molecular weight polyisocyanate, for example with a molecular weight less than about 1000 D. This may comprise the polyisocyanate used to cap the polyols. This low molecular weight polyisocyanate may be present in an amount ranging from 1% to 5% of the composition. The capped polyol can be multifunctional, and typically at least partially trifunctional or higher. The polyol may be any of various biocompatible substances such as polyethylene oxide, polypropylene oxide, polyethylene glycol, and copolymers of these. In one embodiment, the polyol has about 10% to about 30% by weight propylene oxide subunits, and the rest ethylene oxide.

In one embodiment, the polyisocyanate is typically difunctional. In one embodiment, the composition is a fast reacting formulation comprising an aromatic diisocyanate such as toluene diisocyanate. In another embodiment, the low reacting formulations comprise an aliphatic diisocyanate such as isophorone diisocyanate. The polymerization time can be adjusted by selection of appropriate molecular weight polyols. The higher molecular weight polyols produce lower viscosity capped reaction products and faster reacting solutions. Combinations of the above species are considered to comprise a single component when they are stable and remain homogenous while stored at room temperature.

The tissue reactive component of a single-component in situ curing implant is typically called a prepolymer. The cure times of a prepolymer achieved using the approaches described above depend, in part, on controlling one or more of the rate of water diffusion into the prepolymer, the rate of isocyanate to amine conversion, and the activity of the isocyanate-functionalized ends. There are various non-tissue-reactive additions to the prepolymer that can be made at the time of application to speed prepolymer curing. For example, when water is added to the prepolymer just before application, the cure time dependence on water diffusion is reduced. Generally, addition of water in volumetric ratios of approximately 1:1 volumetric ratio with the prepolymer maximally reduces cure time. When additional water is added, such as 4:1 volumetric ratio of water to prepolymer, the cure time increases from its fastest mixed cure time because the polymer density decreases. Similarly, when using higher concentrations of prepolymer, such at 80% or more by volume, the cure time increases from its fastest cure time because the water availability decreases. However, all mixtures with water, from 1% up to about 95% by volume, cure faster than application of prepolymer placed directly on tissue.

In one embodiment, cure times can span as long as 1 hour and as short as 30 seconds, although longer cure times are possible. In general, access will have been made to the implantation site, and preparation of the implantation site completed before the liquid implant is prepared. In one embodiment, the liquid implant is prepared by mixing between two syringes bridged by a female-to-female luer lok connection prepolymer in one syringe and saline or other suitable aqueous solution in the other syringe. In one embodiment, the hydrophilic nature of the prepolymer achieves homogenous mixing in approximately 10 mix cycles for mix ratios of 10-90% prepolymer. In one embodiment, all implant ratios are homogenous after 20 mix cycles. In one embodiment, the fastest cure time are achieved where the mix ratio is approximately 1:1. However, the cure time does not differ by more than 100% for all mix ratios.

The surgeon typically requires a cure time long enough to mix and inject the liquid implant and short enough to provide for in situ curing within a few minutes after implantation. In one embodiment, the cure time ranges from 1 to 10 minutes, such as from 3 to 5 minutes. In one embodiment, the cure time halves for every 10 degree centigrade increase in mixture temperature. The typical difference between body temperature and room temperature is about 10° C. Often, there is a decrease in cure time once the liquid implant is injected in the body.

The first action of water with an isocyanate capped prepolymer is to convert some of the active isocyanate ends on the isocyanate capped polyol and some of the active isocyanate ends on the free isocyanate to amine groups. Amine groups react with other isocyanate groups to cause rapid chain extension and eventual crosslinking. Therefore, reduced cure times can also be achieved by substituting some or all of the water admixture with aqueous amines. However, in the case of the admixture of tissue reactive amines such a mixture is no longer considered a single-component implant.

In one embodiment, the prepolymer is an aromatic isocyanate made by end capping a deionized, dried polyalkylene diol with toluene diisocyanate (TDI), and then reacting the end-capped diol with a deionized dried triol. In one embodiment, the diol is a polyethylene glycol/polypropylene glycol co-polymer (random, block or graft), with EO (ethylene oxide) and PO (propylene oxide) in weight ratios ranging from about 95:5 to about 25:75, e.g., about 75% EO and 25% PO. An exemplary triol is trimethylol propane (TMP). An exemplary composition is the reaction product of from about 25% to 35% TDI, from about 65% to 75% diol (75% EO: 25% PO) and from about 1% to about 8% TMP. In one embodiment, the composition is the reaction product of about 30% TDI, about 70% of the 75:25 diol, and about 1% to about 2% TMP. The prepolymer can have a mean molecular weight of 4500 to 5500 Dalton.

These prepolymers can have the added advantage of being water-soluble. Their water solubility enables them to be injected into tissue to polymerize the tissue; or, alternatively or additionally to solidify as gels to stabilize tissue or structures. The prepolymer acts as a self-sealing fluid when injected into body cavities.

Isocyanate-capped polyols, while suitable, are not the sole adhesives or in situ curing non-adhesive compositions that can be used. In one embodiment, the adhesive is hydrophilic and water-soluble before being crosslinked. This hydrophilicity can enable the adhesive to be injected into tissue to polymerize in contact with, and bond to, the tissue, as adhesive and/or as local bulking agent to fill gaps or fissures, or to stabilize implants. The adhesive can act as a self-sealing fluid when injected into cavities or gaps. Once cured in situ, the hydrophilic adhesive can absorb fluid from the tissue, forming a structure that will be at least somewhat gel-like in character. The cured adhesive can swell to a controlled extent, exerting a controlled amount of local pressure. The tensile properties of the cured adhesive can be adjusted so that the adhesive, like the native tissues of the annulus or of the nucleus, deforms under pressure while exerting a restorative force on the surrounding structures. Hence, the adhesive-tissue composite tends to return to its original shape and location after movement of the spine and is characteristically elastic. These properties can be controlled by the composition of the adhesive, or by providing a controlled degree of dilution with saline at the time of administration. This is in contrast with rigid materials, which tend to fracture rather than yield, and to flowable media, which have no tendency to return to their original shape after relaxation of stress. In particular, hydrophobic adhesives tend to become rigid, favoring fracture of the cured adhesive at the surface of the tissue or implant. They also tend not to bond to tissue, which is highly hydrophilic.

In situ polymerization of a liquid nucleus implant can comprise two phase changes. The first phase change is the conversion of the liquid implant into an elastic solid, e.g., a relatively low modulus gel. In one embodiment, the gel modulus ranges from 0.5 to 20 MPa, from 0.5 to 10 MPa, from 0.5 to 5 MPa, from 1 to 5 MPa, from 1 to 3 MPa, or from 1.5 and 3 MPa. The suitability of the implant modulus is somewhat dependent upon the size of the otomy (surgically created opening) made in the annulus or vertebral body in order to deliver the liquid implant. The larger the otomy, the higher is the minimum acceptable modulus. The minimum acceptable modulus is also determined by the extent of tissue bonding achieved by the implant curing, the higher the bond strength the lower the minimum acceptable modulus.

The second phase change is the conversion of part of the liquid implant into a gas phase, which when released and entrapped during curing results in an elastic gel foam. In one embodiment, the ratio of gas phase to gel phase volume is 10 to 0.1, e.g., 5 to 0.5, or 3 to 1. The gas phase component of the curing implant can ensure intimate contact between implant and surrounding tissue, and specifically the reduction or elimination of air pockets or the need for elaborate venting aspects of the delivery means to accomplish the same.

The uncured liquid implant can be polymeric in nature, as opposed to being a low molecular weight monomer before curing, such as a cyanoacrylate. A number of known polymers are potentially useful in the synthesis of suitable adhesive prepolymers. The polymers can be hydrophilic, for example, sufficiently hydrophilic to swell in water. A suitable range of swelling can be, at atmospheric pressure, between from 5% to about 100%, and more typically is from about 5% to about 30%. In one embodiment, the prepolymers are sufficiently hydrophilic to have substantial solubility in water, such as, for instance, 1 g/l or more, e.g., 10 g/l or more, or 100 g/l or more.

The cured implant may be stable in the body, or may degrade in the body to smaller, excretable molecules ("degradable"). A wide variety of linkages are known to be unstable in the body. These include, without limitation, esters of hydroxy acids, particularly alpha and beta hydroxy carboxylic acids; esters of alpha and beta amino acids; carboxylic acid anhydrides; phosphorous esters; and certain types of urethane linkages. In one embodiment, the cured implant is stable in the body for prolonged periods, as the fibrous materials of the annulus have very limited self-repair capabilities, and the nucleus has virtually none. However, if methods are found to enhance natural biological repair of the nucleus or annulus, then degradable adhesives or fillers could be used.

The prepolymers can also have reactive groups covalently attached to them, or part of the backbone. The reactive groups are suitable for reaction with tissue, and for crosslinking in the presence of water or components of bodily fluids, for example water and protein. Suitable groups include isocyanate, isothiocyanate, anhydrides and cyclic imines (e.g., N-hydroxy succinimide, maleimide, maleic anhydride), sulfhydryl, phenolic, polyphenolic, and polyhydroxyl aromatic, and acrylic or lower alkyl acrylic acids or esters. Such reactive groups are most commonly bonded to a preformed polymer through suitable linking_groups in the polymer. Commonly found linking_groups include, without limitation, amines, hydroxyls, sulfhydryls, double bonds, carboxyls, aldehydes, and ketone groups. Of these groups, aliphatic hydroxyls are among the most widely used.

Thus, suitable base polymers include poly(alkyl)acrylic acids and polyhydroxyalkyl acrylates, polysaccharides, proteins, polyols, including polyetherpolyols, polyvinyl alcohol, and polyvinylpyrrolidone, and these same structures with amine or sulfur equivalents, such as polyethyleneimine, aminosugar polymers, polyalkylamine substituted polyethers, and others. Any of these polymers can be substituted with two or three reactive groups, as is required to form a crosslinkable polymer. When there are many substitutable linking groups, as with polysaccharides, only a few of the substitutable groups (here, mostly hydroxyls) should be substituted, and the derivatized polymer will have a somewhat random substitution. In one embodiment, the hydrophilic polymer will have only a few substitutable linking groups. Polyether polyols grown on glycol or amine starters will typically have reactive groups only at the end of the polyether chains, allowing for detailed control of stoichiometry. Such polymers can be used. In one embodiment, the base polymer is a polymer of ethylene glycol, or a copolymer of ethylene glycol with one or more of propylene glycol, butylene glycol, trimethylene glycol, tetramethylene glycol, and isomers thereof, wherein the ratio of ethylene glycol to the higher alkanediol in the polymer is sufficient to provide substantial water solubility at room or body temperature. Such polymer substrates can be synthesized by known methods. More typically, preformed polyetherpolyols are purchased, optionally in a prequalified medical grade, from any of numerous catalogs or manufacturers.

In one embodiment, the prepolymer comprises a polyisocyanate-capped polymeric polyol and a small amount of free poly isocyanate. Such materials and their synthesis are described in detail in U.S. Pat. No. 6,524,327, the disclosure of which is incorporated herein by reference. The small amount of excess polyisocyanate, typically of molecular weight less than about 1000 Daltons, maximizes the reactivity of the polyols, and by directly and rapidly reacting with tissue, promotes bonding of the adhesive to tissue. Typically the small isocyanate contains up to about 3% of the number of active isocyanate groups on the polymer. The small isocyanate may be all or part low molecular weight capped diol. The capped polyol is multifunctional, and typically is trifunctional or tetrafunctional, or a mixture of trifunctional and/or tetrafunctional with difunctional. The polyol can be at least in part a polyether polyol as described above.

The polyisocyanate is typically difunctional, but tri- or tetrafunctional, or star, forms of isocyanate are known and can be useful. Branching (tri- or tetra-functionality) may be provided by a trifunctional polymer, or by providing a tri- or tetrafunctional low molecular weight polyol, such as glycerol, erthyritol or isomer, or trimethylolpropane (TMP). Fast reacting formulations use an aromatic diisocyanate such as toluene diisocyanate. Slow reacting formulations use an aliphatic diisocyanate such as isophorone diisocyanate. Many additional diisocyanates are potentially useful. Some are listed in U.S. Pat. No. 6,524,327, and these and others are found in chemical catalogs, for example from Aldrich Chemical. Alternatively, the polymerization time can be adjusted by selecting appropriate molecular weight polyols. The higher molecular weight polyols produce lower viscosity capped reaction products and slower reacting solutions. However, at any molecular weight of the polyol(s), the reaction rate is most significantly determined by the reactivity of the functional end group attached to the polyol.

In one embodiment, the prepolymer is liquid at room temperature (ca. 20° C.) and body temperature (ca. 37° C.), for ease of administration and of mixture with additives, etc. The prepolymer is stable in storage at room temperature, when protected from moisture and light.

The prepolymer may be supplemented by the addition, during manufacture or at the time of administration, of ancillary materials. These may include reinforcing materials, drugs, volume or osmotic pressure controlling materials, and visualization aids for optical, fluoroscopic ultrasound or other visualization of fill locations. Reinforcing materials may include particulate materials, fibers, flocks, meshes, and other conventionally used reinforcers. These can be commercial materials approved for in vivo medical use. Visualization materials include a wide variety of materials known in the art, such as, among others, small particles of metals or their oxides, salts or compounds for fluoroscopy, gas-filled particles for ultrasound, and dyes or reflecting particles for optical techniques.

Osmotic properties can be adjusted for immediate or long-term effects. In one embodiment, the polyether polyol isocyanates have little ionic charge either before or after polymerization. However, in some situations, as described below, it is desirable to have a controlled degree of swelling in water after curing. This can be controlled in part by the ratio of ethylene glycol to other polyols in the formulation. It can also be adjusted by adding charged groups to the formulation. A simple method is to add charged polymers or charged small molecules to the adhesive at the time of application, for example dissolved in an aqueous solution. Charged polymers, such as polyacrylic acids, will react poorly with the isocyanates, but will tend to be trapped in the polymerized matrix. They will tend to increase the swelling of the cured material. In turn, this would allow the use of higher proportions of non-ethylene glycol monomers in the polyols. Alternatively, charge could be introduced by addition of hydroxy carboxylic acids, such as lactic acid, or tartaric acid, during synthesis or during administration. Added polymers could instead be polyamines, but, to avoid rapid polymerization, should be tertiary or quaternary amines or other amine types that will not react with isocyanate. A method of increasing swelling is to incorporate higher concentration of diffusible ions, such as soluble salts—e.g., sodium chloride—into the adhesive at the time of application. The salt will attract water into the adhesive polymers; after polymerization, the salt will diffuse away and the gel will remain expanded.

The prepolymer can be adjusted in several ways to optimize its post-cure properties for the particular situation. In one embodiment, a method of adjustment of properties is dilution of the polymer with water, saline, or other aqueous solution. A typical dilution would be in the range of 5% or less (volume of saline in liquid polymer), for formation of dense, high-tensile, low-swelling deposits, up to about 95% (19 vol. saline/vol. polymer) for readily swelling, highly compliant deposits or bonds. In formulation, allowance should be made for the amount of water that will flow into the adhesive from the tissue during reaction. This will usually be relatively small for bulk deposits, but is of more concern for thin adhesive layers. In thin layers, fast-curing compositions can be used, such as compositions with a higher proportion of aromatic diisocyanates. In general, dilution will reduce the tensile strength and the modulus. The amount of dilution will tend to be different depending on whether the modulus or tensile strength is to match that of the annulus (higher) or the nucleus (lower).

Various non-reactive ingredients can be added to the polymer solution either in the prepolymer or in the aqueous solution to alter the hydrogel mechanical properties, e.g., tensile strength, elasticity and bubble size. Inert particulate such as tantalum powder will result in bubble nucleation and a finer bubble size, increase the modulus of the hydrogel, and make the hydrogel radio opaque. Emulsifiers can be added to increase mix homogeneity, reduce bubble size, and provide a higher elongation at break. It is possible to use the same diol used to construct the prepolymer as an emulsifier. Alternatively, a higher or lower molecular weight diol may be used. The ratio of EO/PO can be altered to increased mixability, or pure forms of EO or PO can be used.

Other adjustable factors include the molecular weight of the polymer, and its degree of branching; and its hydrophilicity, which is a function of the particular polyol or polyols used in the formulation. In addition, additives, as described above, can also influence these properties.

Compositions

One embodiment provides a liquid preparation for use in medicine, and its uses therein. The liquid preparation contains a reactive polymer, which comprises a "base polymer" or "backbone polymer", reactive groups on the backbone polymer, and a slight excess of "free" (low molecular weight) polyreactive molecules. The liquid composition is prepared by a method requiring no catalysts and essentially no solvent. The reactive liquid polymer is self-curing when applied to tissue, by absorption of water and other reactive molecules from the tissue. The cured polymer is used to seal tissue to tissue, or to devices; to apply a protective coating to tissue; to form an implant within or upon tissue; to deliver drugs. The cured polymer is optionally provided with biodegradable groups, and has a controllable degree of swelling in bodily fluids.

Backbone Polymers

The backbone polymer will comprise a polymeric segment, of molecular weight about 500 D or more, e.g., about 1000 to about 10,000 D, or up to about 15 kD or 20 kD. The backbone polymer will contain groups that can be easily derivatized ("capped") to form the final reactive group. Such groups can be alcohols or amines, or optionally sulfhydryls or phenolic groups. Examples include polymers such as a polymeric polyol, or optionally a polymeric polyamine or polyamine/polyol. In one embodiment, the polyols are polyether polyols, such as polyalkylene oxides (PAOs), which may be formed of one or more species of alkylene oxide. The PAO, when comprising more than one species of alkylene oxide, may be a random, block or graft polymer, or a polymer combining these modes, or a mixture of PAO polymers with different properties. Exemplary alkylene oxides are ethylene oxide and propylene oxide. Other oxiranes may also be used, including butylene oxide. PAOs are typically made by polymerization onto a starter molecule, such as a low molecular weight alcohol or amine, e.g., a polyol. Starting molecules with two, three, four or more derivatizable alcohols or other derivatizable groups can be used. The multi-armed PAOs obtained from such starters will typically have one arm for each group on the starter. PAOs with two, three or four terminal groups can be used. Mixtures of PAOs or other backbone polymers, having variable numbers of arms and/or variation in other properties, are contemplated.

Common polyols useful as starters are aliphatic or substituted aliphatic molecules containing a minimum of 2 hydroxyl or other groups per molecule. Since a liquid end product is desired, the starters can be of low molecular weight containing less than 8 hydroxyl or other groups. Suitable alcohols include, for illustration and without limitation, adonitol, arabitol, butanediol, 1,2,3-butanetriol, dipentaerythritol, dulcitol, erythritol, ethylene glycol, propylene glycol, diethylene glycol, glycerol, hexanediol, iditol, mannitol, pentaerythritol, sorbitol, sucrose, triethanolamine, trimethylolethane, trimethylolpropane. Small molecules of similar structures containing amines, sulfhydryls and phenols, or other groups readily reactive with isocyanates, are also useable.

The PAO, or other backbone polymer, may optionally incorporate non-PAO groups in a random, block or graft manner. In particular, non-PAO groups are optionally used to provide biodegradability and/or absorbability to the final polymer. Groups providing biodegradability are well known. They include hydroxy carboxylic acids, aliphatic carbonates, 1,4-dioxane-2-one (p-dioxanone), and anhydrides. The hydroxy carboxylic acids may be present as the acid or as a lactone or cyclic dimmer, and include, among others, lactide and lactic acid, glycolide and glycolic acid, epsilon-caprolactone, gamma-butyrolactone, and delta-valerolactone. Amino acids, nucleic acids, carbohydrates and oligomers thereof can be used to provide biodegradability. Methods for making polymers containing these groups are well known, and include, among others reaction of lactone forms directly with hydroxyl groups (or amine groups), condensation reactions such as esterification driven by water removal, and reaction of activated forms, such as acyl halides. The esterification process involves heating the acid under reflux with the polyol until the acid and hydroxyl groups form the desired ester links. The higher molecular weight acids are lower in reactivity and may require a catalyst making them less desirable.

The backbone polymers may also or in addition carry amino groups, which can likewise be functionalized by polyisocyanates. Thus, the diamine derivative of a polyethylene glycol could be used. Low molecular weight segments of amine containing monomers could be used, such as oligolysine, oligoethylene amine, or oligochitosan. Low molecular weight linking agents, as described below, could have hydroxyl functionality, amine functionality, or both. Use of amines will impart charge to the polymerized matrix, because the reaction product of an amine with an isocyanate is generally a secondary or tertiary amine, which may be positively charged in physiological solutions. Likewise, carboxyl, sulfate, and phosphate groups, which are generally not reactive with isocyanates, could introduce negative charge if desired. A consideration in selecting base polymers, particularly other than PAOs or others that react only at the ends, is that the process of adding the reactive groups necessarily requires adding reactive groups to every alcohol, amine, sulfhydryl, phenol, etc. found on the base polymer. This can substantially change the properties, particularly the solubility properties, of the polymer after activation.

Reactive Groups

The base or backbone polymer is then activated by capping with low molecular weight (LMW) reactive groups. In one embodiment, the polymer is capped with one or more LMW polyisocyanates (LMW-PIC), which are small molecules, typically with molecular weight below about 1000 D, more typically below about 500 D, containing two or more reactive isocyanate groups attached to each hydroxyl, amine, etc of the base molecule. After reaction of the LMW-PIC with the backbone, each capable group of the backbone polymer has been reacted with one of the isocyanate groups of the LMW-PIC, leaving one or more reactive isocyanates bonded to the backbone polymer via the PIC. The LMW-PIC are themselves formed by conjugation of their alcohols, amines, etc. with suitable precursors to form the isocyanate groups. Starting molecules may include any of those mentioned above as starting molecules for forming PAOs, and may also include derivatives of aromatic groups, such as toluene, benzene, naphthalene, etc. Exemplary LMW-PIC for activating the polymer are diisocyanates, e.g., particular toluene diisocyanate (TDI) and isophorone diisocyanate, both commercially available. When a diisocyanate is reacted with a capable group on the base polymer, one of the added isocyanates is used to bind the diisocyanate molecule to the polymer, leaving the other isocyanate group bound to the polymer and ready to react. As long as the backbone polymers have on average more than two capable groups (hydroxyl, amine, etc.), the resulting composition will be crosslinkable.

A wide variety of isocyanates are potentially usable as LMW-PICs. Suitable isocyanates include 9,10-anthracene diisocyanate, 1,4-anthracenediisocyanate, benzidine diisocyanate, 4,4'-biphenylene diisocyanate, 4-bromo-1,3-phenylene diisocyanate, 4-chloro-1,3-phenylene diisocyanate, cumene-2,4-diisocyanate, cyclohexylene-1,2-diisocyanate, cyclohexylene-1,4-diisocyanate, 1,4-cyclohexylene diisocyanate, 1,10-decamethylene diisocyanate, 3,3'dichloro-4,4'biphenylene diisocyanate, 4,4'diisocyanatodibenzyl, 2,4-diisocyanatostilbene, 2,6-diisocyanatobenzfuran, 2,4-dimethyl-1,3-phenylene diisocyanate, 5,6-dimethyl-1,3-phenylene diisocyanate, 4,6-dimethyl-1,3-phenylene diisocyanate, 3,3'-dimethyl-4,4'diisocyanatodiphenylmethane, 2,6-dimethyl-4,4'-diisocyanatodiphenyl, 3,3'-dimethoxy-4,4'-diisocyanatodiphenyl, 2,4-diisocyantodiphenylether, 4,4'-diisocyantodiphenylether, 3,3'-diphenyl-4,4'-biphenylene diisocyanate, 4,4'-diphenylmethane diisocyanate, 4-ethoxy-1,3-phenylene diisocyanate, ethylene diisocyanate, ethylidene diisocyanate, 2,5-fluorenediisocyanate, 1,6-hexamethylene diisocyanate, isophorone diisocyanate, lysine diisocyanate, 4-methoxy-1,3-phenylene diisocyanate, methylene dicyclohexyl diisocyanate, m-phenylene diisocyanate, 1,5-naphthalene diisocyanate, 1,8-naphthalene diisocyanate, polymeric 4,4'-diphenylmethane diisocyanate, p-phenylene diisocyanate, 4,4',4''-triphenylmethane triisocyanate, propylene-1,2-diisocyanate; p-tetramethyl xylene diisocyanate, 1,4-tetramethylene diisocyanate, toluene diisocyanate, 2,4,6-toluene triisocyanate, trifunctional trimer (isocyanurate) of isophorone diisocyanate, trifunctional biuret of hexamethylene diisocyanate, and trifunctional trimer (isocyanurate) of hexamethylene diisocyanate.

In general, aliphatic isocyanates will have longer cure times than aromatic isocyanates, and selection among the various available materials will be guided in part by the desired curing time in vivo. In addition, commercial availability in grades suitable for medical use will also be considered, as will cost. Toluene diisocyanate (TDI) and isophorone diisocyanate (IPDI) can be used. The reactive chemical functionality of the liquid implants can be isocyanate, but may alternatively or in addition be isothiocyanate, to which all of the above considerations will apply.

Physical Properties

The polymerizable materials are typically liquids at or near body temperature (i.e., below about 45 deg. C.), and can be liquid at room temperature, ca. 20-25 deg. C., or below. The liquids are optionally carriers of solids. The solids may be biodegradable or absorbable. The liquid polymerizable materials are characterized by polymerizing upon contact with tissue, without requiring addition of other materials, and without requiring pretreatment of the tissue, other than removing any liquid present on the surface(s) to be treated. A related property of the polymerizable materials is that they are stable for at least 1 year when stored at room temperature (ca. 20-25 degrees C.) in the absence of water vapor. This is because the material has been designed so that both the reaction that polymerizes the polymers, and the reactions that optionally allow the polymer to degrade, both require water to proceed.

In contrast to previous formulations, the polymeric polyisocyanates contain a low residual level of low molecular weight (LMW) polyisocyanates (PIC). For example, the final concentration of LMW-PIC isocyanate groups in the formulation, expressed as the equivalent molarity of isocyanate groups attached to LMW compounds, is normally less than about 1 mM (i.e., 1 mEq), e.g., less than about 0.5 mEq and or less than about 0.4 mEq. In one embodiment, the level of LMW isocyanate groups is finite and detectable, for example greater than about 0.05 mEq, or greater than about 0.1 mEq. In one embodiment, a low but finite level of LMW-PIC molecules tends to promote adherence between the applied polymer formulation and the tissue being treated. However, decreased levels of LMW-PIC may tend to decrease tissue irritation during application and cure of the liquid polymer preparation. In one embodiment, the range of about 1 mEq to about 0.05 mEq is approximately optimal. In situations requiring tissue adherence in the presence of biological fluid, or in adherence to difficult tissues, greater levels of LMW-PIC isocyanate groups may be used.

Swellabilit

The active prepolymers may form intertwined polymer chains after reaction that may change their intertwined geometry under action by fluids within the body. In particular, one or more components may cause the formed polymeric material, whether as coating, adhesive, or solid, to swell. Swelling may have several consequences, and can be controlled. In one mode, swelling can lead to subsequent break-up (physical disintegration) of an implant or other final form, rendering the entire implant absorbable. Or, one or more of the components may dissolve in the body rendering the remaining components absorbable. (Dissolvable materials could be added as solids, or as nonreactive polymers diluting the reactive components.) Or, one or more components may be biodegradable rendering the remaining components absorbable. For example, liquids containing a polyethylene/polypropylene random coblock polyol capped with polyisocyanate are capable of forming elastic gels with water content as high as 90%. When these polyethylene/polypropylene polyols are esterified with a carboxylic acid and reacted with a trifunctional molecule such as trimethylolpropane, or alternatively when the trifunctional molecule is esterified and reacted with diols of polyethylene/polypropylene, useful activated polyols are formed. These polyols, when end capped with a polyisocyanate are capable of forming gels or solids in a living organism that decrease in volume and strength over time.

However, the ratio of propylene oxide to ethylene oxide can be varied, and the two monomers can be polymerized into block copolymers, random copolymers, or graft copolymers. These types are commercially available. While the ethylene oxide groups tend to absorb water, and so to swell the crosslinked material formed in the body, the propylene oxide groups are less hydrophilic, and tend to prevent swelling in aqueous fluids. Thus, the degree of swelling of the polymerized material in water can be controlled by the design of the reactive polymers. Another route of swelling control is by incorporation of non-PAO groups, such as aliphatic or aromatic esters, into the polymer (as, or in addition to, esters used to confer degradability.)

The prepolymer can be formed by capping the polyols (as backbone polymer) with polyisocyanate, preferably a diisocyanate. However, suitable isocyanates have the form $R(NCO)_x$, where x is 2 to 4 and R is an organic group. Another approach to creating an in situ polymerizing liquid that biodegrades in the body is to graft the polyol onto a biodegradable center. Suitable polymers for inclusion as center molecules are described in U.S. Pat. No. 4,838,267. They include alkylene oxalates, dioxepanone, epsilon-caprolactone, glycolide, glycolic acid, lactide, lactic acid, p-dioxanone, trimethylene carbonate, trimethylene dimethylene carbonate and combinations of these.

The center molecule may be a chain, a branched structure, or a star structure. Suitable star structures are described in U.S. Pat. No. 5,578,662. Isocyanate capped alkylene oxide can be reacted with these molecules to form one or more extended chains. The ends of these chains can therefore participate in crosslinking with other centers or bond to tissue.

Center molecules such as those listed above will form rigid solids upon polymerization. Therefore, it is generally more useful to ensure at least 80% alkylene oxide is in the final polymerized structure. Furthermore, the alkylene oxide should be comprised of at least 70% ethylene oxide.

These criteria ensure that the polymerized product is flexible enough to prevent stress localization and associated tissue bond failure. Furthermore, star molecules in general will not be preferred since they contain numerous branches. More numerous branching of the center molecule is associated with higher liquid viscosity. Furthermore, highly branched prepolymers will form polymerized products more slowly and with higher modulus. For example, U.S. Pat. No. 5,578,662 quotes a cross-linking reaction time of 5 minutes to 72 hours. Both of these characteristics are undesirable when the prepolymer is intended as a surgical adhesive or sealant.

Absorbable Compositions and Particulate Additives

Absorbable prepolymer systems can be composed of discontinuous (solid) and continuous (liquid) parts. The solid part may be absorbable or may not be absorbable. One of the simplest forms of an absorbable implant is one that mechanically breaks into small pieces without appreciable chemical modification. Fracture of an implant can be seeded or propagated by the placement of hard centers in the polymer during formation.

Mixing the liquid polymer with calcium triphosphate particles will after exposure to fluids or tissue polymerize into an elastic solid containing an inelastic particulate. Movement of the surrounding tissue will deform the elastic implant. Since the particulate cannot deform, stress will localize around these centers and cracks will begin to propagate from these centers. In this way, the rate of disintegration and size of the disintegrated parts can be controlled by varying the particulate size, the modulus of the formed continuous polymer, and the density distribution of the particulate.

Non-absorbable solids are well known and include, as examples and without limitation, calcium triphosphate, calcium hydroxylapatite, carbon, silicone, Teflon, polyurethane, acrylic and mixture of these. Absorbable solids are well known and include, as examples and without limitation, glycolic acid, glycolide, lactic acid, lactide, dioxanone, epsilon-caprolactone, trimethylene carbonate, hydroxybutyrate, hydroxyvalerate, polyanhydrides, and mixtures of these.

Other absorbable prepolymer liquids can be composed of two continuous mechanically mixed parts. For example, one part may be absorbable and the other not. Consequently, the absorption of one part results in the mechanical disintegration or weakening of the implant. Absorbable components may include liquid forms of cellulose ether, collagen, hyaluronic acid, polyglycolic acid, glycolide and others known in the art.

Exemplary Polymeric Structures

There are several ways in which the above-recited steps can be used to obtain a liquid reactive polymer system. In a simple system, a polymeric polyol with a number of end groups on average greater than two is treated with a slight excess of a LMW-PIC, such as toluene diisocyanate. The reaction product is formed under nitrogen with mild heating, preferably by the addition of the LMW-PIC to the polymer. The product is then packaged under nitrogen, typically with no intermediate purification.

In one embodiment, the biodegradable polyol composition includes a trifunctional hydroxy acid ester (e.g., several lactide groups successively esterified onto a trifunctional starting material, such as trimethylolpropane, or glycerol). This is then mixed with a linear activated polyoxyethylene glycol system, in which the PEG is first capped with a slight excess of a LMW-PIC, such as toluene diisocyanate. Then the activated polymer is formed by mixing together the activated polyoxyethylene glycol and the lactate-triol. Each lactate triol binds three of the activated PEG molecules, yielding a prepolymer with three active isocyanates at the end of the PEG segments, and with the PEG segments bonded together through degradable lactate groups. In the formed implant, the lactate ester bonds gradually degrade in the presence of water, leaving essentially linear PEG chains that are free to dissolve or degrade. Interestingly, in this system, increasing the percentage of degradable crosslinker increases rigidity, swell and solvation resistance in the formed polymer.

Other polyol systems include hydroxy acid esterified linear polyether and polyester polyols optionally blended with a low molecular weight diol. Similarly, polyester and polyether triols esterified with hydroxy acid are useful. Other polyol systems include the use of triol forming components such as trimethylolpropane to form polyols having three arms of linear polyether chains.

Delivery Devices and Methods

In one embodiment, the delivery device possesses a blocking component for preventing liquid implant from escaping from the nuclear region of a vertebral disc and preferably prevents liquid implant from coating a portion or all of the otomy made to access the nuclear region. The delivery device can be used in combination with a hollow fixed instrument that guides the operational instruments to a selected location in or adjacent to an annular fissure, or other site in the spine in need of repair. The described procedures address minimally invasive use, but can be used in open surgeries. A detailed description of an entire apparatus or series of apparatuses for each instance should not be necessary to enable those skilled in the art to make a device for the treatment methods disclosed herein, since some of the individual components are conventional. The methods can be accomplished with endoscopic instruments, automated surgical systems, or any system with structural parts that function as set forth herein.

Delivery Device

Figure 2:
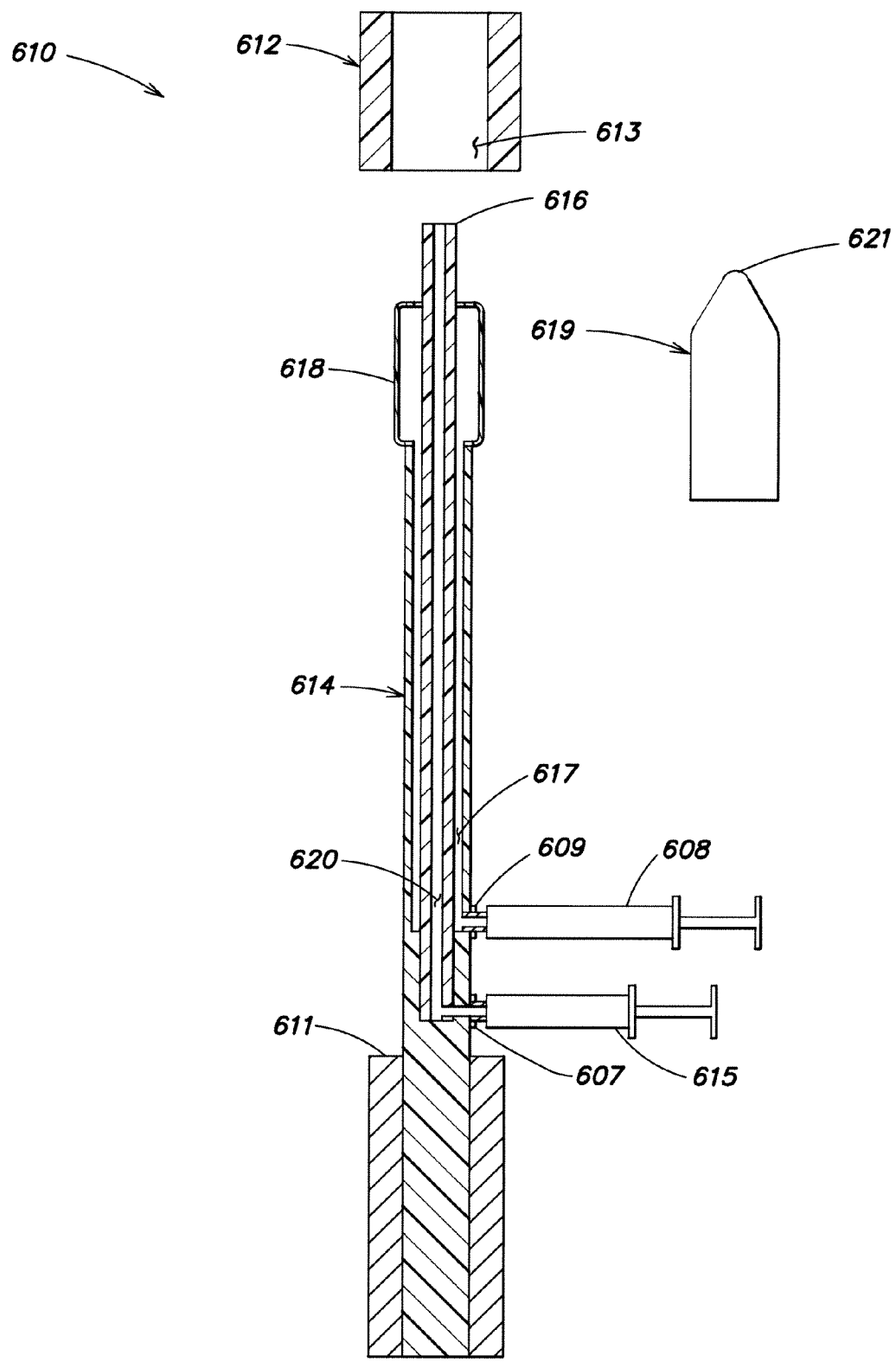
FIG. 2 is a schematic view of an introducer and an embodiment of a delivery catheter having a balloon as a blocking component, in which solid lines illustrate the position of the instrument in the absence of bending forces and dotted lines indicate the position of the distal portion of the instruments under bending forces applied to the intradiscal section of the instrument.

In one embodiment, a device for delivering the liquid nucleus implant to the site is an injector. An example of a suitable delivery device 610 is shown in a schematic way (not to scale) in FIG. 2. The device illustrated is constructed in the same general manner as an intravascular catheter, although it may be considerably shorter in overall length. FIG. 2 shows the handle 611, which holds a catheter-like compound tube 614, which in this embodiment encloses an injection lumen 620 terminating at distal tip 616, and an inflation lumen 617 terminating in encircling balloon 618. The injection lumen connects to a port 607 near to or within the handle 611 for connecting a polymer source 615, which as illustrated can be a syringe, but could instead be a pump. The balloon 618 and tube 614, when being introduced into the patient, passes through the lumen 613 of an introducer 612. The balloon 618 can be arranged in a collapsed state to facilitate the introduction into lumen 613. The introducer 612 can be as simple as a hollow tube. An introducer can comprise a hollow tube device 612 or a combination of a simple exterior cannula 612 that fits around a tapered obturator 619. A hollow tube is placed through skin and tissue to provide access into the annulus fibrosus. More complex variations exist in percutaneous instruments designed for other parts of the body and can be applied to design of instruments intended for disc repairs. The distal end 621 of the introducer will typically be inserted into tissue until it lies at a location into which the prosthetic is to be formed. A suitable outer diameter for the tube portion 612 is in the range of 5 to 12 mm. In the illustrated embodiment, the diameter of the collapsed balloon 618 is less than the inner diameter of the tube portion 613.

In one embodiment, the blocking component is tapered distally such that a wider part of the blocking component projects into the nuclear space with a diameter greater than the diameter of the opening in the annulus.

In one embodiment, the pressure and/or delivery volume of the liquid implant is controlled. Control of injection can be provided by placing a pressure transducer in a suitable location. With pumps, a pressure sensor can be placed on or in the tube, or at the tip. With a syringe, a pressure-sensitive pad can be placed on the proximal end of the plunger, as well as on the tube or in the tip. A pressure sensor can be coupled to a display, or a gauge, and/or can be coupled to a microprocessor for automatic or semiautomatic control. In the later case, the variance of pressure with time can be used to help decide when injection has been sufficient.

Figure 3:
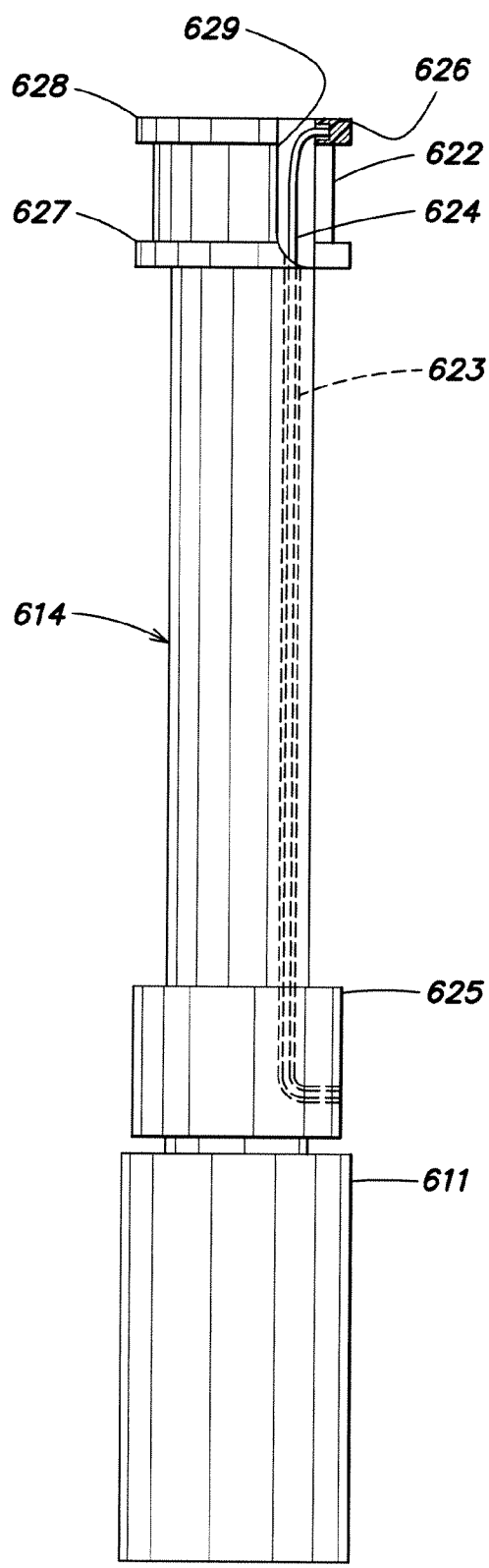
FIG. 3 is a schematic view of another embodiment of a delivery catheter in which the blocking component comprises an elastic collar.

The delivery device described above uses a balloon to be inflated in a cannula 612 or a surgically formed otomy to provide a barrier to implant loss during injection of the liquid nucleus implant into the disc nuclear region. The balloon is inflated by attaching an air source 608 to a port 609 located on the catheter-like compound tube 614. Alternatively, the blocking means may be any mechanically distensible interface that forms a seal between it and a cannula or surgically formed passageway. An example of an alternative blocking means is illustrated in FIG. 3. In this instance, the blocking means 622 replaces the balloon 618 of FIG. 2. The inflation lumen 617 of FIG. 2 is replaced by wire lumen 623. Inside wire lumen 623 is wire 624 attached to actuation hub 625. When actuation hub 625 is turn axially the wire 624 is drawn into the hub. The detailed mechanics for achieving this wire retraction are known in the art. Blocking means 622 is comprised of an elastic material with outer diameter less than the inner diameter 613 of the cannula 612 of FIG. 2. Blocking means 622 possesses a concentric axially aligned hole 626 of inner diameter equal to the outer diameter of catheter 614. The blocking means 622 resides on the delivery catheter 614 as shown in FIG. 3. The blocking means 622 is held in place by stationary hub 627 and actuation hub 628. A slot 629 in tube 614 allows wire 624 to pull actuation hub 628 toward actuation hub 625. The actuation hub 625 is rotatable on catheter 614 such that when tension is placed on wire 624 the blocking means 622 compresses and increases in outer diameter.

In one embodiment, the blocking means 622 prevents liquid implant from leaving the injection site. The proximal end of the blocking component can be flush with the inner layers of the annulus. To accomplish this the catheter 614 may be marked for imagining during fluoroscopy to indicate the proximal and distal ends of the blocking means. In another embodiment, the blocking component has a tissue engaging surface to prevent slippage.

In the use of some liquid nucleus implants, primarily those that are not foaming, in one embodiment a third lumen is provided in the delivery catheter to allow for the passage of displaced air as the nuclear space is filled with implant.

In the application of multiple injections the inflation lumen 617 may be filled with a disposable lumen that can be removed after a first application of liquid implant without repositioning the blocking means and inflation lumen 617. In this case, the disposable lumen can be extended beyond the catheter tip 616 to provide a first small application of liquid implant to coat the inner surface of the annulus, such a disposable lumen can be flexible to contour to and spread evenly liquid implant upon the inner surface of the annulus.

Methods

There are two common approaches to a vertebral disc. The posterior approach is generally an open procedure, where access to the disc does not require a cannula or tube through which surgical procedures are performed. The contra-lateral approach is generally a percutaneous approach where access to the disc requires a cannula or tube through which surgical procedures are performed. The methods associated with each of these approaches are different, but both approaches use the delivery catheters disclosed herein.

The proximal approach is used when the disc annulus has large defects or the disc is impinging on the spinal cord. In this case the outer dimension of the balloon when inflated should exceed the expected inner diameter of the otomy to be made in the disc annulus so that a sealed interface can be formed between balloon and annulus. The diameter of the balloon will typically be between 5 and 12 mm. The balloon may have a rigid maximum diameter when inflated or may be elastic.

The balloon shape may be dumbbell in axial cross section to help localize it in the otomy of the annulus.

The procedural steps are as follows: 1) surgically expose the portion of the disc annulus to be treated, 2) create an otomy in the annulus sufficient to allow for removal of part or all of the disc nucleus to prevent further loss of disc nucleus in the case of an annulus defect and to reduce pressure on the annulus in the case of a herniated disc, 3) insert the delivery catheter so that the blocking means is flush with the excavated inner surface of the nucleus/annulus interface, 4) actuate the blocking means so that the delivery catheter is localized in the annulus, 5) begin injecting nucleus implant to a desired volume or pressure, 6) hold assembly in place until the implant has cured, and 7) deactuate the blocking means and remove the delivery catheter. Generally the otomy will be left open so that the annulus may heal and seal the implant within the disc.

The contra-lateral approach is generally a percutaneous approach. It is used when the annulus has a normal shape and generally when a nuclectomy is performed. In the diagnostic phase leading up to the decision to place a nucleus implant first the integrity of the annulus is assessed. This is done by placing an anchoring guidewire through the annulus wall into the nucleus of the disc so that various diagnostic and treatment procedures may be performed. The guidewire may be employed in directing an injection needle for delivering an indicator solution to the nucleus to assess leakage outside the annulus from the nucleus. Alternatively the guidewire may be employed in directing means for creating an otomy in the annulus and subsequent removal of nucleus.

Figure 4A:
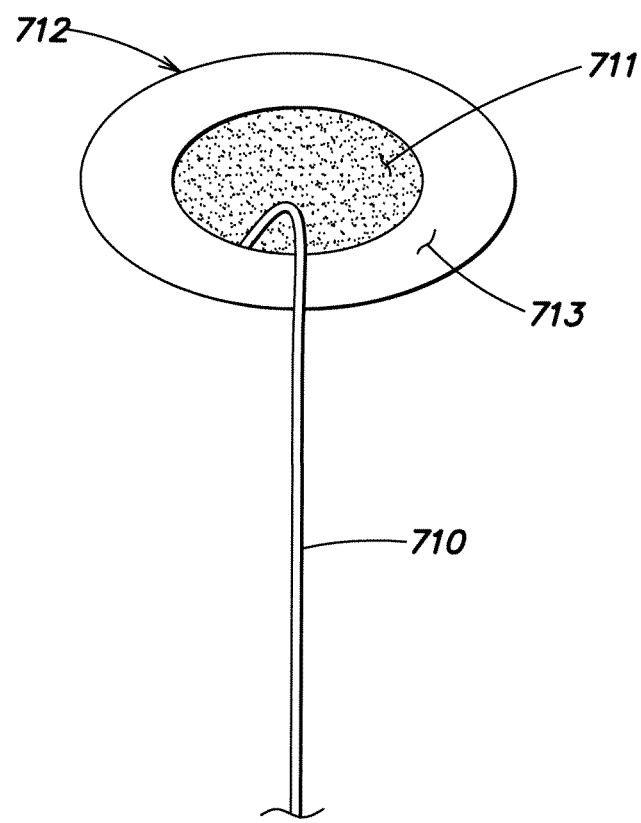
FIG. 4A is a schematic view of a guidewire introduced into the nuclear disc space.
Figure 4B:
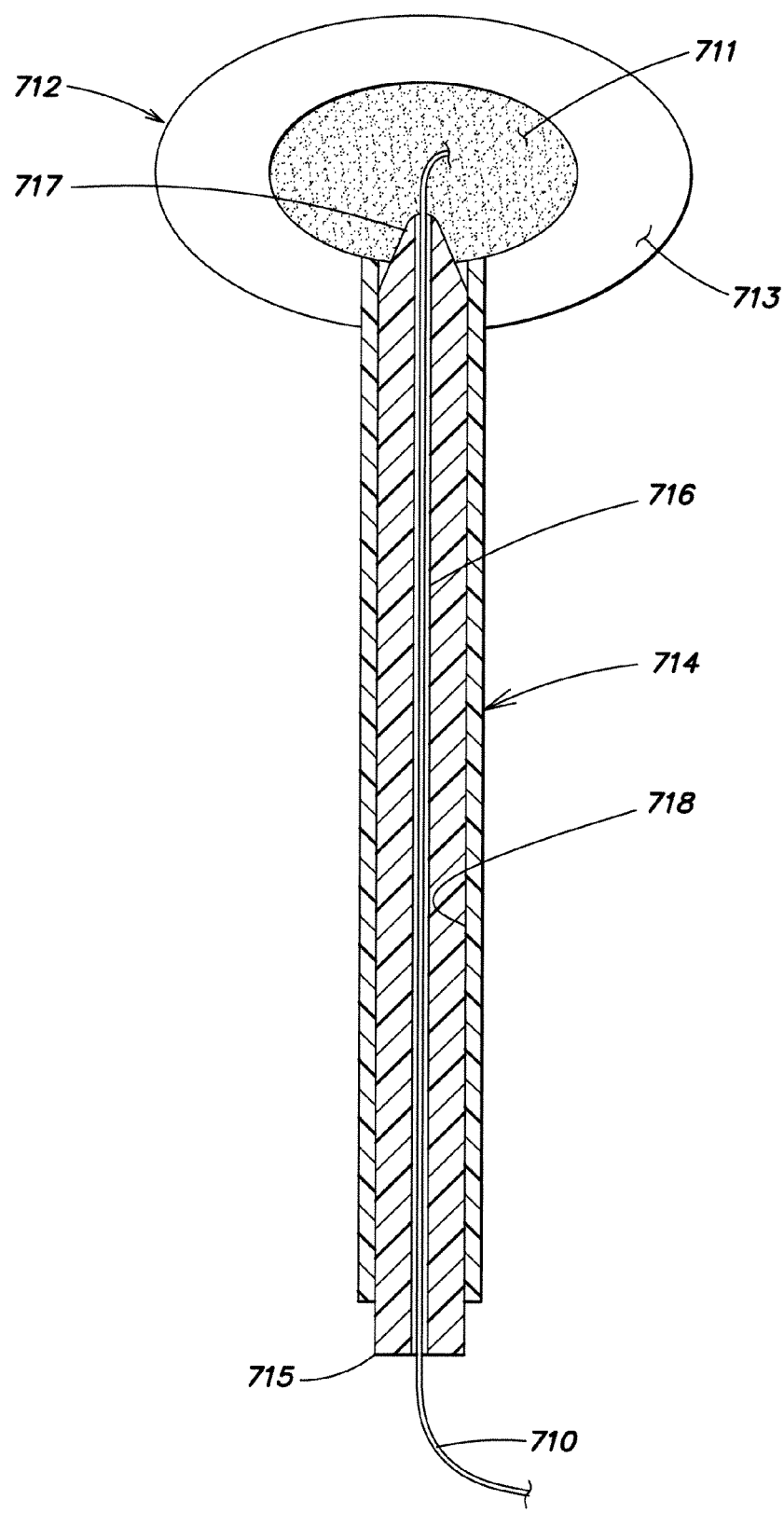
FIG. 4B is a schematic view of a cannula fitted with an obturator introduced into the nuclear disc space.
Figure 4C:
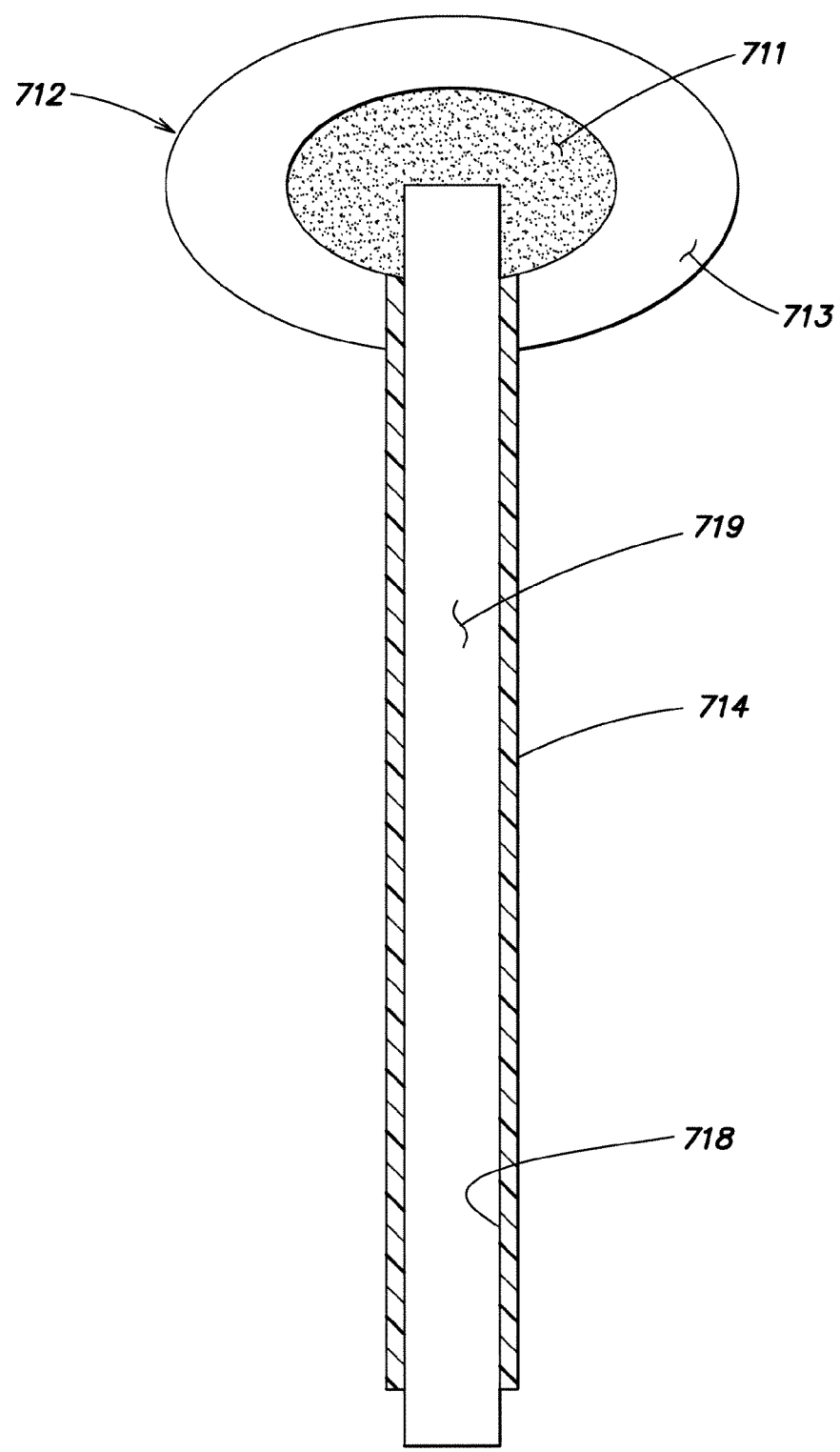
FIG. 4C is a schematic view of a shaver blade introduced into the lumen of the cannula of FIG. 4B.
Figure 4D:
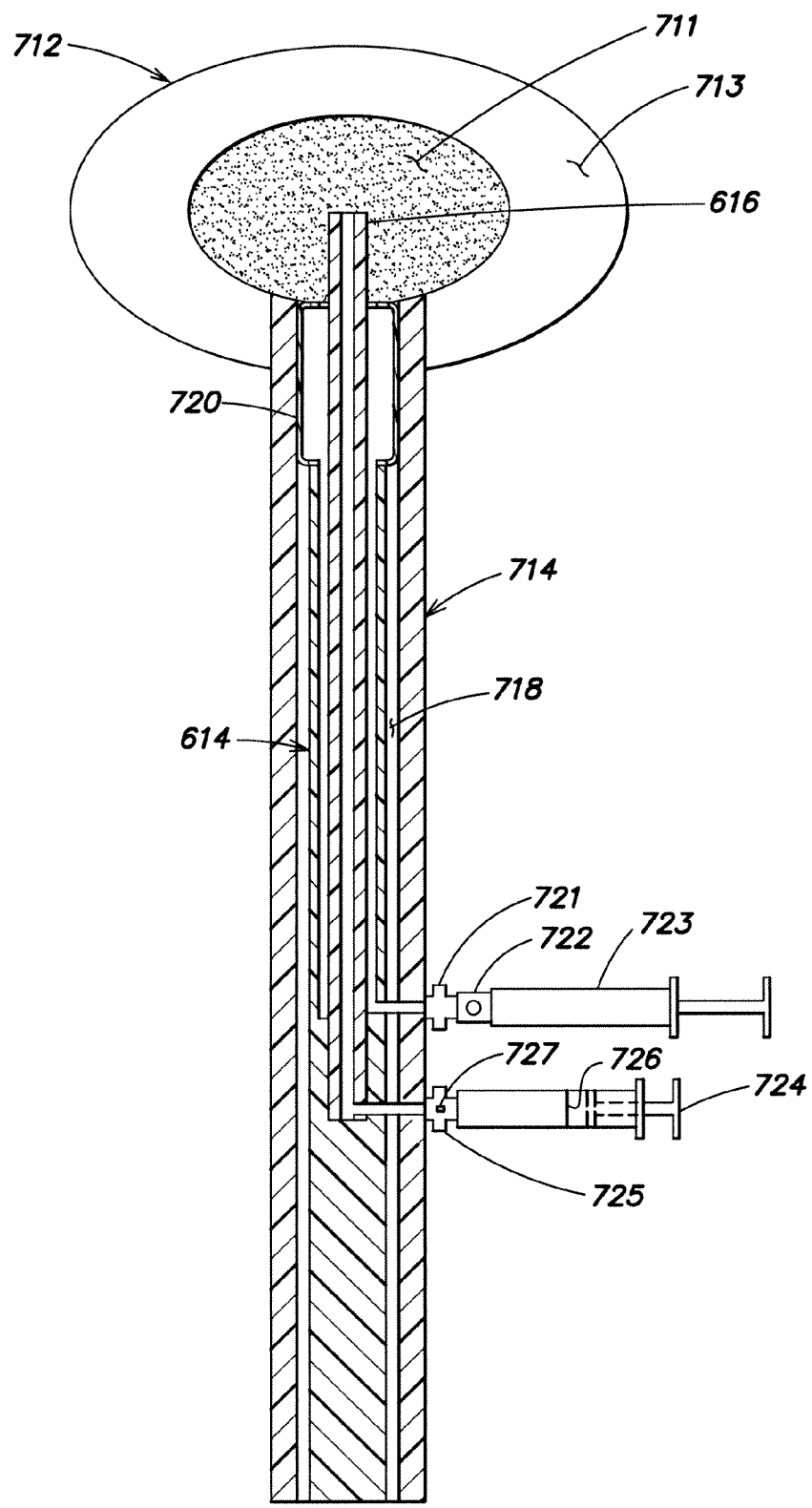
FIG. 4D is a schematic view of a delivery catheter introduced into the lumen of the cannula of FIG. 4B.

In the contra-lateral procedure described here, the guidewire is further employed to deliver a cannula. In FIG. 4A, cranial view, a guidewire 710 is position in the nuclear area 711 of a disc 712. The nuclear area may include part of the disc annulus 713. FIG. 4B shows a cannula 714 fitted with an obturator 715 with a central axial bore 716. The distal end of the guidewire 710 is placed into the bore 716 and the cannula/obturator assembly is advanced along the guidewire 710. The proximal end 717 of the obturator 715 is tapered such that it easily enters the disc annulus 713 with a minimal disruption of tissue. The annulus 713 may be prepared for this operation by placing a slit cut in the annulus centered on the guidewire. Under fluoroscopy the cannula 714 is advanced into the annulus until its proximal end is flush with the outer layers of the disc nucleus 711. The outer diameter of the cannula 714 is preferably 5 mm. The obturator 715 is removed and a 4.5 mm shaver blade 719 is introduced into the lumen 718 of the cannula 714 as pictured in FIG. 4C. The nucleus is then removed to a therapeutic degree and the evacuated space washed of loose debris. The delivery catheter 614 is introduced into the lumen 718 of the cannula 714 as shown in FIG. 4D. The proximal end of the catheter is positioned flush with the periphery of the evacuated space of the nucleus and the blocking means 720 actuated. If the blocking means is a balloon as shown in FIG. 4D, then a stop-cock 721 is attached to inflation port 722 and to the open end of the stopcock is connected to a syringe 723 loaded with either air or liquid. The balloon is inflated by positioning the valve of the stop-cock so that pressure applied to the syringe 723 delivers fluid volume to the balloon. When the proper volume of fluid is delivered or an appropriate pressure achieved the valve of the stop-cock is closed fixing the balloon 720 in a deployed position. The syringe 724 containing the single-part liquid implant is attached to the delivery catheter via luer connection 725. The delivery catheter is primed by depressing the plunger of syringe 724 to a specified volume position 726 indicated on the syringe. The medical professional may optionally release the catheter balloon and subsequently re-inflate to allow for the volume displaced by priming the catheter to be released from the nucleus of the disc 711. Then liquid implant from syringe 724 is injected into the nuclear space 711 until a specified volume or pressure is achieved. The dispensing syringe 724 may optionally have a pressure sensing device 727. After a specified period of time the balloon 720 is deflated and the delivery catheter 614 removed. A plurality of delivery catheters may be deployed in this manner to fills regions left unfilled, or to build pressure in the nuclear space 711 by injecting liquid implant inside of an already formed implant volume. This may optionally be performed by a piercing needle placed in the center of a formed implant, and additional liquid implant dispensed into this center. The liquid implant delivered in this manner would not require a blocking mechanism since the formed implant provides the blocking means.

Figure 5:
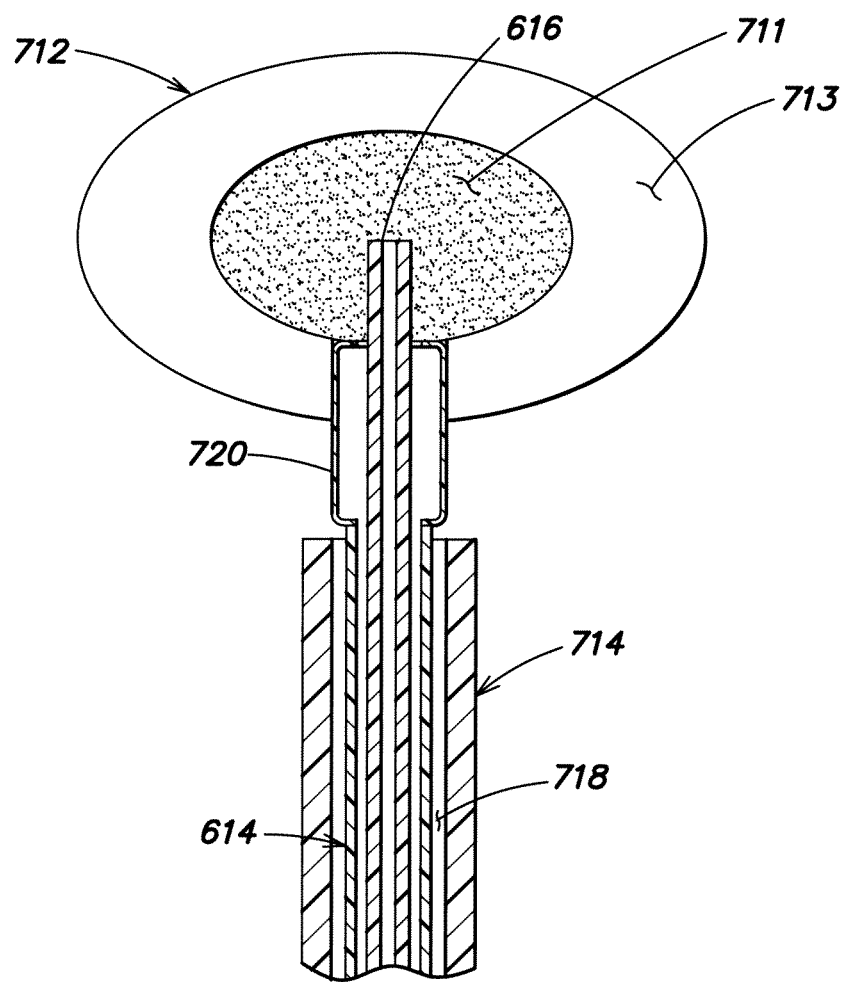
FIG. 5 is a schematic view of a cannula moved distally in the annulus such that the delivery catheter is deployed in contact with the annulus tissue.

Optionally, the cannula 714 may be moved distally in the annulus as depicted in FIG. 5, such that the delivery catheter 614 may be deployed in contact with the annulus tissue 713 and inflated there to provide blockage.

The invention claimed is:

1. A method for treating a defect in a spinal disc nuclear space, comprising:
 (a) creating an opening by open, percutaneous or laparoscopic techniques to access the defect in the nuclear space;
 (b) removing a desired amount of tissue from the nuclear space;
 (c) positioning a delivery catheter through the opening;
 (d) fluidically isolating the nuclear space by blocking the opening with a blocking component of the catheter;
 (e) preparing an in-situ curable liquid material comprising a prepolymer comprising a polymeric polyol end-capped with diisocyanate, and a low molecular weight polyisocyanate;
 (f) delivering the in-situ curable liquid material through a lumen of the catheter to the nuclear space; and
 (g) curing the in-situ curable liquid material by adding an aqueous solution to the nuclear space.

2. The method of claim 1, further comprising:
 (h) removing the blocking component and the delivery catheter; and
 (i) closing the opening.

3. The method of claim 1, where the treating comprises one or more of:
 (i) augmenting or replacing the nucleus pulposus;
 (ii) reinforcing a wall of the annulus fibrosus;
 (iii) removing and sealing herniated or bulging portions of a disc; and
 (iv) closing a defect in the annulus pulposus.

4. The method of claim 1, wherein the removing in (b) comprises removing one of (i) a portion of the nucleus pulposus, (ii) all of the nucleus puplosus, or (iii) a portion or all of the nucleus pulposus and a portion or all of the inner layers of the annulus fibrosus.

5. The method of claim 1, wherein the blocking component comprises an expandable balloon surrounding the catheter.

6. The method of claim 1, wherein the blocking component comprises an elastic collar surrounding the catheter.

7. The method of claim 1, wherein after (e) a second in-situ curable liquid material is delivered over or into said first cured material, to achieve a desired pressure in the nuclear space.

8. The method of claim 1, wherein the blocking component isolates the tissues surrounding the opening in the annulus from the liquid implant placed in the nuclear space to provide for the unobstructed growth of the annulus into the space created by the opening.

9. The method of claim 1, wherein the blocking component is tapered distally such that a wider part of the blocking component projects into the nuclear space with a diameter greater than the diameter of the opening in the annulus.

10. The method of claim 1, wherein the blocking component has a tissue engaging surface to prevent slippage.

11. The method of claim 1, wherein the curable liquid material is delivered under pressure sufficient to increase the distance between vertebral endplates adjacent to a treated nucleus.

12. The method of claim 11, wherein a lumen in the delivery catheter allows for evacuation of gas from the nuclear space as liquid implant is injected.

13. The method of claim 1, wherein a disposable lumen is placed inside the delivery catheter lumen to allow for multiple injections of liquid implant without repositioning the blocking component of the delivery catheter.

14. The method of claim 1, wherein the delivering of the curable liquid material in (d) comprises:
   a first application that coats and seals an inner surface of the annulus fibrosus; and
   a second application to fill the nuclear space.

15. The method of claim 14, wherein the second application pressurizes the nuclear space.

16. The method of claim 1, wherein the curable liquid material foams while it cures and produces a pressure inside the nuclear space independent of the pressure of the delivering.

17. The method of claim 1, wherein the curable liquid material foams and incorporates any air pockets remaining in the nuclear space to provide substantially complete contact between the inner surface of the annulus and the cured implant.

18. The method of claim 1, wherein after (b), a sheet is interposed between the nuclear space and the blocking component to provide increased strength to the cured liquid implant after it has cured.

19. The method of claim 18, wherein the sheet is a mesh.

20. The method of claim 18, wherein the sheet comprises a cured liquid implant.

21. The method of claim 18, wherein the sheet has a conical cross section.

22. The method of claim 1, wherein the polymeric polyol comprises polyethylene oxide and polypropylene oxide.

23. The method of claim 22, wherein the polymeric polyol comprises polyethylene oxide in an amount ranging from 70 to 90% by weight and polypropylene oxide in an amount ranging from 10 to 30% by weight.

24. The method of claim 1, wherein the polymeric polyol comprises 75% polyethylene oxide and 25% polypropylene oxide.

25. The method of claim 1, wherein the prepolymer is a trifunctional polyol capped with diisocyanate, the trifunctional polyol being formed by trimerizing polymeric diols with trimethylol propane.

26. The method of claim 1, the prepolymer has a molecular weight ranging from 4500 D to 5500 D.

27. The method of claim 1, the low molecular weight polyisocyanate has a molecular weight of 1000 D or less.

* * * * *